(12) United States Patent
Matzger et al.

(10) Patent No.: US 7,429,238 B2
(45) Date of Patent: Sep. 30, 2008

(54) SYSTEMS AND METHODS FOR THE GENERATION OF CRYSTALLINE POLYMORPHS

(75) Inventors: Adam J. Matzger, Ann Arbor, MI (US); Meidong Lang, Ann Arbor, MI (US); Kibum Kim, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 478 days.

(21) Appl. No.: 10/269,190

(22) Filed: Oct. 11, 2002

(65) Prior Publication Data

US 2003/0113802 A1 Jun. 19, 2003

Related U.S. Application Data

(60) Provisional application No. 60/329,403, filed on Oct. 15, 2001, provisional application No. 60/329,351, filed on Oct. 15, 2001, provisional application No. 60/329,476, filed on Oct. 15, 2001.

(51) Int. Cl.
C40B 30/10 (2006.01)
C40B 30/00 (2006.01)
G01N 33/53 (2006.01)
A61K 9/00 (2006.01)

(52) U.S. Cl. .............................. 506/12; 506/7; 424/400; 435/7.1

(58) Field of Classification Search .................... 506/12, 506/7; 435/7.1; 424/400
See application file for complete search history.

(56) References Cited

U.S. PATENT DOCUMENTS

| | | | | |
|---|---|---|---|---|
| 4,344,934 A | * | 8/1982 | Martin et al. ................ | 514/462 |
| 4,880,623 A | * | 11/1989 | Piergiorgio et al. ......... | 514/356 |
| 5,859,258 A | * | 1/1999 | Breen et al. .................. | 548/252 |
| 5,980,942 A | * | 11/1999 | Katzhendler et al. ........ | 424/465 |
| 2002/0006443 A1 | * | 1/2002 | Curatolo et al. ............. | 424/486 |
| 2002/0048610 A1 | * | 4/2002 | Cima et al. .................. | 424/725 |
| 2003/0170309 A1 | * | 9/2003 | Babcock et al. ............. | 424/486 |

FOREIGN PATENT DOCUMENTS

GB    2 139 892 A  * 11/1984

OTHER PUBLICATIONS

Lang et al., J. Am. Chem. Soc. 2002, 124, 14834-14835.*
Price et al., J. Am. Chem. Soc. 2005, 127, 5512-5517.*
Beckmann, Organic Process Research & Development (Aug. 2000), vol. 4, 372-383.*
McPherson, J. Crystal Growth (1992) 122, pp. 161-167.*
Otsuka et al., Chem. Pharm. Bull., 45:894 [1997].
Otsuka et al., J. Pharm. Sci., 84:614 [1995].
Wong and Mitchell, Int. J. Pharm., 88:261 [1992].
Weissbuch et al., Acta Crystallogr. Sect. B-Struct. Sci. 51:115 [1995].
Sun and Grant, Pharm. Res., 18:274 [2001].
Kobayashi et al., Int. J. Pharm. 193:137 [2000].
Lisgarten et al., J. Crystallographic and Spectroscopic Res. 19:641 [1989].
Colfen et al., Langmuir 14:582-589 [1998].
Qi et al., Angew Chem Int. Ed. 39:604-607 (2000).
Staab et al., Adv. Materials 2:40-43 (1990).
Weissbuch et al., Adv.Materials 12:952-956 (1994).
Saujanya et al., Polymer 42:2255-2258 (2001).
Stupp J. Biomed. Matl. Res. 26:169-183 (1992).
Weissbuch et al., Science 253:637-745 (1991).
Davey et al., J. Am. Chem. Soc., 119:1767-1772 (1997).
Benton et al., Faraday Discuss, 95:281-297 (1993).
D'Souza et al., Nature 398:312-316 (1999).
DiMartino et al., Int. J. Pharmaceutic 128:1-8 (1996).
El-Said, S.T.P. Pharma. Sci., 5:232-237 (1995).
Coelin et al., J. Pharm. Sci. 86:1062 (1997).
Rodriquez and Murphy, J. Pharm. Sci. 88:651 (1999).

* cited by examiner

Primary Examiner—Mark L Shibuya
(74) Attorney, Agent, or Firm—Casimir Jones S.C.

(57) ABSTRACT

The present invention relates to systems and methods for generating polymorphs of compounds. In particular, the present invention provides high throughput systems and methods for generating and identifying new crystalline polymorphs that find use as improved drugs, pigments, explosives, nonlinear optical crystals, solid-state reactive compounds, and other polymorphic materials.

25 Claims, 2 Drawing Sheets

SYSTEMS AND METHODS FOR THE GENERATION OF CRYSTALLINE POLYMORPHS

The present application claims priority to U.S. Provisional Pat. Appln. Nos. 60/329,403, 60/329,351, and 60/329,476, each of which was filed on Oct. 15, 2001, and each of which is herein incorporated by reference in their entireties.

FIELD OF THE INVENTION

The present invention relates to systems and methods for generating polymorphs of compounds. In particular, the present invention provides high throughput systems and methods for generating and identifying new crystalline polymorphs that find use as improved drugs, pigments, explosives, nonlinear optical crystals, solid-state reactive compounds, and other polymorphic materials.

BACKGROUND OF THE INVENTION

Pharmaceutical companies expend much of their resources in attempts to find new blockbuster drugs (greater than $1 billion/year sales) (D. Eric Walters, BC 5220, Techniques in Biomedical Research, "The Rational Basis of Drug Design"). In order to be successful, a new drug should satisfy several criteria: safe to use; effective for the intended use; stable (chemically and metabolically); good solubility profile; synthetically feasible; and novel (i.e., patentable). An important aspect of drug development is the identification of leads. A lead is any chemical compound that shows the biological activity sought. A lead is not the same as a drug however as it should meet the criteria listed above prior to use as a drug. There are two broad tasks in drug discovery. The first is lead-finding. Here the task is to find a chemical compound that has a desired bioactivity. The second is lead-optimization, modifying the lead structure to build in the other desirable properties (safety, solubility, stability, etc.).

There are many ways to find lead compounds. In the beginning, plants and other natural products were the source of most medicinal substances. As the science of medicinal chemistry evolved, it was discovered that the plants and natural products contained specific compounds that are responsible for the therapeutic effect. It became possible to isolate the active components, so that dosage could be more accurately regulated.

Other medicines came about because of accidental observations and discoveries (e.g., penicillin). The discovery of penicillin led to a large-scale screening effort, in which thousands of soil microorganisms were grown and tested to see whether they could produce other substances that kill bacteria. Antibiotics such as streptomycin, neomycin, gentamicin, erythromycin, and the tetracyclines resulted from these efforts.

Chemical modification of known drugs can often lead to improved drugs. For example, naturally occurring penicillin G is broken down by bacterial beta-lactamases. Addition of two —$OCH_3$ groups produces methicillin, which is resistant to lactamase. Another example of chemical modification is found in the opiate analgesics. The parent compound is morphine, which occurs in opium poppies. Morphine is a powerful analgesic, but it has serious side effects: respiratory depression, constipation, and dependence liability. Thousands of analogs (related chemical structures) have been synthesized in an effort to find analgesics with lower incidence of side effects. In some cases, small changes in chemical structure may have a big influence on the activity. For example, nalorphine is a partial agonist (shows some morphine-like activity, and at higher concentration, antagonizes morphine effects), and naloxone is an antagonist. Considerable simplification of the molecule is possible. For example, meperidine has only two rings instead of four, but it maintains strong analgesic activity. It has better oral absorption than morphine, and shows less GI side effects. Methadone is an analgesic in which the original piperidine ring (6-membered ring containing a nitrogen atom) is completely absent. It retains analgesic activity, has good oral activity, and has a long half-life in the body. Dextromethorphan is constructed on a mirror image of the morphine ring system. It has no opiate analgesic effects or side effects, but is a useful anti-tussive agent.

Some drugs are discovered by observing side effects of existing drugs. For example, minoxidil was found to grow hair on bald men as a side effect in a study of its antihypertensive effects. Viagra's effect on penile dysfunction was discovered in clinical trials for treatment of angina; it had originally been designed as an antihypertensive drug.

In the modern era, most leads are discovered using various screening processes. For example, over a couple of decades, the National Cancer Institute has put hundreds of thousands of different chemical compounds through a battery of anti-cancer assays. Current screening assays often employ miniaturization and automation with robots for high throughput screening, allowing hundreds of thousands of compounds to be screened in a short period of time.

Structure-based molecular design is yet another method to identify lead molecules for drug design. This method is based on the premise that desired drug candidates possess significant structural and chemical complementarity with their target molecules. This design method can create molecules with specific properties that make them conducive for binding to the target site. The molecular structures that are designed by the structure-based design process are meant to interact with biochemical targets, for example, whose three-dimensional structures are known.

Even with the extensive resources expended in drug discovery and design, there are no systematic methods for generating drugs with desired properties. Thus, the art is in need of additional systems and methods to facilitate the discovery and optimization of therapeutic and other useful compounds.

SUMMARY OF THE INVENTION

The present invention relates to systems and methods for generating polymorphs of compounds. In particular, the present invention provides high throughput systems and methods for generating and identifying new crystalline polymorphs that find use as improved drugs, pigments, explosives, nonlinear optical crystals, solid-state reactive compounds, and other polymorphic materials.

For example, the present invention provides methods for forming and/or identifying polymorphs, comprising: a) providing a sample (e.g., solution, melt, vapor) comprising a compound (e.g., a dissolved compound), and a polymer library comprising two or more different polymers; b) contacting the polymer library with the sample under conditions that promote crystal formation; and analyzing formed crystals for polymorph structure. Any sample that is capable of forming crystals or amorphous phases may be used with the method. In some embodiments, the compound is a drug, including small molecule drugs, as well as more complex molecules such as peptides and proteins.

The present invention is not limited by the number of, or identity of the polymers. The present invention is also not limited by the structure of the polymers and includes polymer films, powder, particles, suspensions, and other forms. Polymers that find use with the present invention include, but are not limited to, acrylonitrile/butadiene/styrene resin, alginic acid (sodium salt), butyl/isobutyl methacrylate copolymer, cellulose acetate, cellulose acetate butyrate, cellulose propionate, cellulose triacetate, ethyl cellulose, ethylene/acrylic acid copolymer, ethylene/ethyl acrylate copolymer, ethylene/propylene copolymer, ethylene/vinyl acetate (14, 18, 25, 28, 33% and 40% VA) copolymer, hydroxybutyl methyl cellulose, hydroxypropyl cellulose, hydroxypropyl methyl cellulose, methyl cellulose, methyl vinyl ether/maleic acid copolymer, methyl vinyl ether/maleic anhydride copolymer, nylon 6, nylon 6/6, nylon 6/9, nylon 6/10, nylon 6/12, nylon 6(3)T, nylon 11, nylon 12, phenoxy resin, polyacetal, polyacrylamide, polyacrylamide carboxyl modified (low), polyacrylamide carboxyl modified (high), poly(acrylic acid), polyamide resin, 1,2-polybutadiene, poly(1-butene) isotactic, poly(n-butyl methacrylate), polycarbonate resin, poly(diallyl isophthalate), poly(diallyl phthalate), poly(2,6-dimethyl-p-phenylene oxide), poly(4,4-dipropoxy-2,2-diphenyl propane fumarate), poly(ethyl methacrylate), polyethylene high density, polyethylene low density, polyethylene chlorinated (25, 36, 42, and 48% chlorine), polyethylene chlorosulfonated, poly(ethylene oxide), polyethylene oxidized, poly(ethylene terephthalate), poly(2-hydroxyethyl methacrylate), poly(isobutyl methacrylate), polyisoprene chlorinated, poly(m-ethyl methacrylate), poly(4-methyl-1-pentene), poly(alphamethylstyrene), poly(p-phenylene ether-sulphone), poly(phenylene sulfide), polypropylene isotactic chlorinated, polypropylene isotactic, polystyrene, polysulfone resin, poly(tetrafluoroethylene), poly(2,4,6-tribromostyrene), poly(vinyl acetate), poly(vinyl alcohol) 100% hydrolyzed, poly(vinyl alcohol) 98% hydrolyzed, poly(vinyl buyral), poly(vinyl chloride), poly(vinyl chloride) 1.8% carboxylated, poly(vinyl formal), polyvinylpyrrolidone, poly(vinyl stearate), poly(vinylidene fluoride), styrene/acrylonitrile copolymer (75/25), styrene/acrylonitrile copolymer (70/30), styrene/allyl alcohol copolymer, styrene/butadiene ABA block copolymer, styrene/butyl methacrylate copolymer, styrene/ethylene-butylene ABA block copolymer, styrene/maleic anhydride copolymer, vinyl alcohol/vinyl butyral copolymer, vinyl chloride/vinyl acetate (10, 12, and 19% VA) copolymer, vinyl chloride/vinyl acetate copolymer 1% carboxylated, vinyl chloride/vinyl acetate/hydroxypropyl acrylate terpolymer, and vinyl chloride/vinyl acetate/vinyl alcohol terpolymer, functionalized polybutadienes, poly(ethylene-co-propylene-co-5-methylene-2-norbornene), poly(perfluoropropylene oxide)-co-poly(perfluoroformaldehyde), metaldehyde, pectic acid, polyethylenimine, poly(ethylene-co-carbon monoxide), poly(3-hydroxybutyric acid), poly(dimethylsiloxane), poly[(dibenzo-18-crown-6)-co-formaldehyde], poly[(phenyl isocyanate)-co-formaldehyde], poly(vinylsulfonic acid), poly(melamine-co-formaldehyde), polyphosphates, polyphosphazenes, tributyltin fluoride, and polysaccharides. In some embodiments, the polymer library comprises three or more different polymers (e.g., 10 or more, 50 or more, etc.). Each polymer location on the library can comprise single polymer types or mixtures of polymers.

In some embodiments, the method further comprises the step of isolating at least one of the formed crystals to prepare bulk amounts (e.g., gram to kilogram) of the crystal. In some embodiments, this involves seeding a solution containing the dissolved compound with one or more of the formed crystals to promote crystal growth. In other embodiments, large surfaces or vessels are associated with the polymer that produced a particular polymorph and the bulk crystals are produced on the polymer.

In some embodiments, the method further comprises the step of formulating the crystals into a pharmaceutical preparation (i.e., a composition configured for pharmaceutical use). In some embodiments, the method further comprises the step of treating a subject (e.g., a human) with the pharmaceutical preparation. In addition to the crystal, the pharmaceutical preparation may contain any number of additional components that facilitate handling or use. Such components are known in the art. In some embodiments, the pharmaceutical preparation includes one or more additional therapeutic compounds.

The present invention also provides polymer libraries for use in the methods above, as well as polymer libraries in combination with crystals and/or solutions. In some embodiments, a high throughput system is provided. For example, polymer libraries comprising tens to hundreds, to thousands of different polymers are provided and exposed to a plurality of different dissolved compounds to identify polymorphs of the crystallized compounds. In some embodiments, the systems comprise an automated liquid handling system for delivering solution to the polymers. In some embodiments, the systems further comprise one or more devices for analyzing formed crystals (e.g., an X-diffraction device).

The systems and methods of the present invention find use in methods for identifying new drugs. For example, pre-existing drugs with a known polymorph are screened by the systems and methods of the present invention to identify novel polymorphs of the drugs. The novel polymorphs may then be analyzed for biological activity, used in Federal Food and Drug Administration (FDA) trials, patented, marketed, and sold. For example, because the novel polymorph is readily characterized (e.g., the structure and method of making can be readily described) and represents a new composition of matter, it is available for patent protection in many countries. This provides an important route for obtaining new patent protection on previously patented drugs. For example, a patented drug may have a known polymorph. New polymorphs identified by the systems and methods of the present invention allow the drug to be patented again in the new form.

In addition to drugs, polymorphs of the present invention find use as improved pigments, explosives, nonlinear optical crystals, solid-state reactive compounds, and other polymorphic materials. For example, the color of a pigment or dye, a key property, can depend on its crystal structure. For example, the industrially important pigment quinacridone exhibits three polymorphic forms, each with a different shade of red. Understanding and control of the pigment has been hampered by inadequate knowledge of the structures (Potts et. al., J. Chem. Soc., Chem. Commun., 2565 [1994]). Nonlinear (NLO) optical and photonic materials are important for applications such as frequency doubling or tripling of laser light, wave mixing, telecommunications, and information processing and computing. Organic and polymeric materials have shown great potential for such applications; these materials work because they exhibit strong nonlinear polarizations in the presence of high intensity electromagnetic fields. The properties and performance of NLO and photonic materials depends critically on their composition, microstructure and purity.

The present invention also provides compositions comprising novel polymorphs identified using the system and methods of the present invention. For example, the present invention provides a composition comprising C-centered monoclinic carbamazepine. In some embodiments, the composition comprises a pharmaceutical preparation (e.g., a tablet). In some embodiments, the C-centered monoclinic carbamazepine is provides with other therapeutic compositions (e.g., other drugs or other polymorphs of carbamazepine). The present invention also provides orthorhombic acetaminophen crystals. The present invention provides systems and methods to prepare such crystals from solution. Thus, in some embodiments, the present invention provides a composition comprising a solution (e.g., an aqueous solution) of dissolved acetaminophen in contact with orthorhombic acetaminophen crystals grown from the solution. In some embodiments, the composition further comprises a polymer in contact with the crystals.

DEFINITIONS

Figure 1:
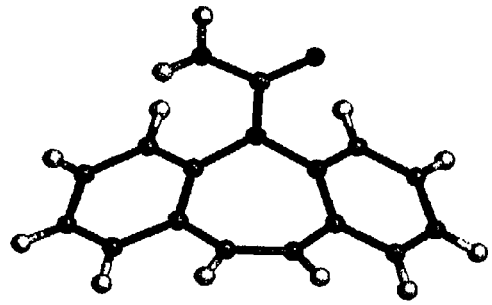
FIG. 1 shows the structure and molecular packing of the C-centered monoclinic polymorph of carbamazepine.
Figure 1:
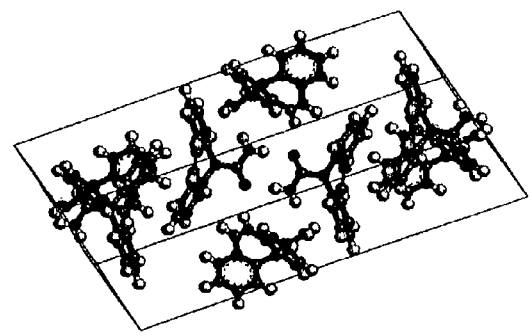

To facilitate an understanding of the present invention, a number of terms and phrases are defined below:

As used herein, the term "polymorph" refers to a crystalline phase of a substance. Many substances feature polymorphism, which is the ability of a substance to exist as two or more crystalline phases that have different arrangements and/or conformations of the molecules in the crystal lattice. As used herein, the term polymorph includes amorphous phases and solvents/hydrates (i.e., psuedopolymorphs).

As used herein, the term "polymer library" refers to a composition comprising a plurality of different polymers positioned in particular locations so as to allow reactions to occur on the polymers at the particular locations. For example, containers or solid surfaces (e.g., plate, glass, metal, or ceramic surfaces, multi-well plates, dishes, vials, tubes, flasks, etc.) with a plurality of different polymers contained in discrete locations of the surface are polymer libraries. For example, a multi-well plate that contains a first polymer in a first well and a second polymer in a second well, etc. provides a polymer library.

As used herein, the term "tabletability" refers to the capacity of a powdered material to be transformed into a tablet of specified strength under the effect of compaction pressure (Joiris et al., Pharm. Res., 15:1122 [1998]). Tabletability describes the effectiveness of the applied pressure in increasing the tensile strength of the tablet and demonstrates the relationship between the cause, the compaction pressure, and the effect, the strength of the compact.

As used herein, the term "compressibility" refers to the ability of a material to undergo a reduction in volume as a result of an applied pressure (Joiris et al., Pharm. Res., 15:1122 [1998]). Compressibility indicates the ease with which a power bed undergoes volume reduction under compaction pressure and is often represented by a plot showing the reduction of tablet porosity with increasing compaction pressure.

As used herein, the term "compactibility" refers to the ability of a material to produce tablets with sufficient strength under the effect of densification (Joiris et al., Pharm. Res., 15:1122 [1998]). Compactibility shows the tensile strength of tablets normalized by tablet porosity. In many cases, the tensile strength decreases exponentially with increasing porosity (Ryshkewitch, J. Am. Cer. Soc., 36:65 [1953]).

DETAILED DESCRIPTION OF THE INVENTION

The present invention relates to systems and methods for generating polymorphs of compounds. In particular, the present invention provides high throughput systems and methods for generating and identifying new crystalline polymorphs that find use as improved drugs, pigments, explosives, nonlinear optical crystals, solid-state reactive compounds, and other polymorphic materials.

For example, the present invention provides libraries of polymers from which crystals are nucleated by exposing solutions (e.g., supersaturated solutions), the melt or vapor of the compound to the polymers. Growth of crystals on a plurality of polymers provides new methods for obtaining desired polymorphs of compounds and for generating previously unidentified polymorphs of compounds. For example, the systems and methods of the present invention have been used to identify a novel polymorph of carbamazepine. The systems and methods have also been used to generate efficient methods for producing orthorhombic acetaminophen from solution. The novel polymorphs identified by the systems and methods of the present invention find use in identifying drugs with enhanced properties, compared to previously available polymorphs of the compound. Thus, the systems and methods of the present invention provide means for finding drug leads and/or optimizing existing drugs.

Many pharmaceutical solids exhibit polymorphism—i.e., the ability of a substance to exist as two or more crystalline phases that have different arrangements and/or conformations of the molecules in the crystal lattice. Because of their structural differences, polymorphs have different solid-state properties. Consequently, polymorphism can exert profound effects on pharmaceutical processing, including, but not limited to, milling, granulation, and tableting (Conte et al., Il Farmaco (Ed. Pr.) 30:194 [1974]; Otsuka et al., Chem. Pharm. Bull., 45:894 [1997]; Otsuka et al., J. Pharm. Sci., 84:614 [1995]; Tuladhar et al., J. Pharm. Pharmacol., 35:269 [1982]; and Wong and Mitchell, Int. J. Pharm., 88:261 [1992]).

Despite the fact that upon dissolution, two polymorphs will yield identical solutions, the crystalline form affects the rate of dissolution, equilibrium solubility, shelf life and ultimately bioavailabilty. This has implications for isolation, clinical trials, and mass production and is therefore an important aspect of creating a viable therapeutic. With a greater number of polymorphs to choose between for a solid dosage, it is more likely that an optimal mixture of properties can be achieved leading to more efficacious drugs.

In its most simple form, the process of crystallization can be considered to start from a supersaturated solution, produced by evaporation, cooling, or addition of a nonsolvent, by formation of nuclei. These species must achieve a sufficient size in order to proceed on to bulk crystals and it is the arrangement of the molecules in these nanometer-sized structures that leads to the macroscopic crystal. Thus the formation of unstable polymorphs can be attributed to their success in forming viable nuclei, a kinetic effect. Additives designed by consideration of functional groups and lattice parameters (derived from diffraction methods) can also interact with these nuclei to stabilize or destabilize them, and this approach of using designed additives has met with success in some cases (Weissbuch et al., Acta Crystallogr. Sect. B-Struct. Sci. 51:115 [1995]; Chen et al., J. Cryst. Growth 144:297 [1994]; and Davey et al., J. Am. Chem. Soc., 119:1767 [1997]). However, this method is best suited for modifying the crystallization behavior of known polymorphs and is not readily adapted to the generation of new forms with unknown lattice parameters.

Even in crystallizations where no additives are used, it is recognized that spontaneous (homogenous) nucleation is not very common, and in most cases impurities on vessel walls function as heteronuclei to induce crystal formation. The reluctance of saturated solutions to undergo homogeneous nucleation can be explained by the energetic barrier to building a species with a high surface area to volume ratio where many of the molecules do not experience the full stabilization of the bulk. A heteronucleus reduces this barrier by providing stabilization of a growing face of the crystal.

The present invention provides systems and methods for utilizing a combinatorial library of functionalized polymers for crystal formation. Both the types of functional groups and the spacing of these groups is altered to produce surfaces that facilitate polymorph generation. By varying these parameters (e.g., systematically) throughout the library, these polymers produce crystal forms without prior knowledge of the polymorph's structure and allow the discovery of new forms of compounds (e.g., pharmaceutical compounds, etc.) with improved properties over previously available structures. Properties that differ among polymorphs include, but are not limited to: packing properties (e.g., molar volume and density, refractive index, electrical conductivity, thermal conductivity, hygroscopicity); thermodynamic properties (e.g., melting and sublimation temperatures, internal [e.g., structural] energy, enthalpy, heat capacity, entropy, free energy and chemical potential, thermodynamic activity, vapor pressure, solubility); spectroscopic properties (e.g., electronic transitions such as ultraviolet to visible absorption spectra, vibrational transitions such as infrared absorption and Raman spectra, rotational transitions such as far infrared and microwave absorption spectra, nuclear spin transitions such as nuclear magnetic resonance spectra); kinetic properties (e.g., dissolution rate, rates of solid state reactions, and stability); surface properties (e.g., surface free energy, interfacial tensions, habit); and mechanical properties (e.g., hardness, tensile strength, compactibility, tableting, handling, flow, and blending) (See e.g., "Polymorphism in Pharmaceutical Solids," ed. Harry G. Brittain, Marcel Dekker, Inc., New York [1999]).

In some embodiments of the present invention, a plurality of polymers are provided with (e.g., placed onto or into) a solid surface or vessel to facilitate high throughput crystal growth and analysis. In some embodiments, the solid surface or vessel is a multi-chamber plate (e.g., a 96-well or 384-well plate). However, the present invention is not limited by the solid surface or vessel employed. As used herein, the terms "solid support" or "support" refer to any material that provides a solid or semi-solid structure with which another material (e.g., a polymer) can be associated. Such materials include smooth supports (e.g., metal, glass, plastic, silicon, and ceramic surfaces) as well as textured and porous materials. Such materials also include, but are not limited to, gels, rubbers, polymers, and other non-rigid materials. Solid supports need not be flat. Supports include any type of shape including spherical shapes (e.g., beads). Materials associated with the solid support may be associated with any portion of the solid support (e.g., may be attached, enclosed, or in contact with an interior portion of a porous solid support material).

The present invention is not limited by the nature of the polymer used to promote crystal growth. In preferred embodiments, the plurality of polymers used in screening methods of the present invention comprise two or more polymers (e.g., three or more, four or more, five or more, . . . , ten or more, . . . , twenty or more, . . . , fifty or more different polymers). The maximum number of polymers employed in the systems and methods of the present invention is constrained only by the availability of polymer materials (i.e., any of the thousands of known polymers may be employed, as well as new polymers that are identified in the future) and by physical and space limitations of the testing area. However, the systems and methods of the present invention may be employed at very large scales. For example, in some embodiments, 384-well plates are used wherein the bottom surface of each well contains a different polymer material. Dozens of such plates may be arranged on shelves and dozens of shelves may be placed in racks. A single laboratory space can hold hundreds of racks. Thus, a single room can house tens of millions of different polymers, wherein a solution with a candidate compound is applied to each of the polymers and crystals are grown and analyzed to identify the properties of the crystals. Further miniaturization allows even more reactions to be run simultaneously in a single run.

While the present invention is not limited by the nature of the polymer, commercially available polymers that find use with the present invention include, but are not limited to, acrylonitrile/butadiene/styrene resin, alginic acid (sodium salt), butyl/isobutyl methacrylate copolymer, cellulose acetate, cellulose acetate butyrate, cellulose propionate, cellulose triacetate, ethyl cellulose, ethylene/acrylic acid copolymer, ethylene/ethyl acrylate copolymer, ethylene/propylene copolymer, ethylene/vinyl acetate (14, 18, 25, 28, 33% and 40% VA) copolymer, hydroxybutyl methyl cellulose, hydroxypropyl cellulose, hydroxypropyl methyl cellulose, methyl cellulose, methyl vinyl ether/maleic acid copolymer, methyl vinyl ether/maleic anhydride copolymer, nylon 6, nylon 6/6, nylon 6/9, nylon 6/10, nylon 6/12, nylon 6(3)T, nylon 11, nylon 12, phenoxy resin, polyacetal, polyacrylamide, polyacrylamide carboxyl modified (low), polyacrylamide carboxyl modified (high), poly(acrylic acid), polyamide resin, 1,2-polybutadiene, poly(1-butene) isotactic, poly(n-butyl methacrylate), polycarbonate resin, poly(diallyl isophthalate), poly(diallyl phthalate), poly(2,6-dimethyl-p-phenylene oxide), poly(4,4-dipropoxy-2,2-diphenyl propane fumarate), poly(ethyl methacrylate), polyethylene high density, polyethylene low density, polyethylene chlorinated (25, 36, 42, and 48% chlorine), polyethylene chlorosulfonated, poly(ethylene oxide), polyethylene oxidized, poly(ethylene terephthalate), poly(2-hydroxyethyl methacrylate), poly(isobutyl methacrylate), polyisoprene chlorinated, poly(methyl methacrylate), poly(4-methyl-1-pentene), poly(alpha-methylstyrene), poly(p-phenylene ether-sulphone), poly(phenylene sulfide), polypropylene isotactic chlorinated, polypropylene isotactic, polystyrene, polysulfone resin, poly(tetrafluoroethylene), poly(2,4,6-tribromostyrene), poly(vinyl acetate), poly(vinyl alcohol) 100% hydrolyzed, poly(vinyl alcohol) 98% hydrolyzed, poly(vinyl buyral), poly(vinyl chloride), poly(vinyl chloride) 1.8% carboxylated, poly(vinyl formal), polyvinylpyrrolidone, poly(vinyl stearate), poly(vinylidene fluoride), styrene/acrylonitrile copolymer (75/25), styrene/acrylonitrile copolymer (70/30), styrene/allyl alcohol copolymer, styrene/butadiene ABA block copolymer, styrene/butyl methacrylate copolymer, styrene/ethylene-butylene ABA block copolymer, styrene/maleic anhydride copolymer, vinyl alcohol/vinyl butyral copolymer, vinyl chloride/vinyl acetate (10, 12, and 19% VA) copolymer, vinyl chloride/vinyl acetate copolymer 1% carboxylated, vinyl chloride/vinyl acetate/hydroxypropyl acrylate terpolymer, and vinyl chloride/vinyl acetate/vinyl alcohol terpolymer, as well as, functionalized polybutadienes, poly(ethylene-co-propylene-co-5-methylene-2-norbornene), poly (perfluoropropylene oxide)-co-poly (perfluoroformaldehyde), metaldehyde, pectic acid, polyethylenimine, poly(ethylene-co-carbon monoxide), poly (3-hydroxybutyric acid) and copolymers with valeric acid, polylactide, polyaminoacids, polyacenaphthylene, poly(dimethylsiloxane), poly[(dibenzo-18-crown-6)-co-formaldehyde] and other polymers containing metal chelating groups, poly[(phenyl isocyanate)-co-formaldehyde], poly(vinylsulfonic acid), poly(melamine-co-formaldehyde), polyphosphates, polyphosphazenes, tributyltin fluoride, polysaccharides, and other organic and inorganic polymers.

Polymers at each location in the library can comprise a mixture of two or more different polymers in one or more different locations. The combination of polymers in different ratios dramatically expands the diversity of conditions available in the libraries.

Solutions containing the compound to be screened are applied to the polymers and incubated under conditions that facilitate crystal growth. The present invention is not limited by the manner in which the compounds are applied to the polymers. In some embodiments, a solution is used to supply each region of a polymer library. Solution may be delivered by pouring, transfer through tubing, injection, or any other means. Where thousands to millions of individual polymers are used, in preferred embodiments, an automated delivery system is used. The present invention is not limited to the use of solutions. Melts of materials and vapors onto the polymers also find use in the system and methods of the present invention.

The solvent used to solubilize any particular compound may be varied. In some embodiments, a variety of solvents are used for each compound, wherein each different solvent type is exposed to each type of polymer to increase the range of crystallization conditions used in the library. In such embodiments, multiple regions (e.g., zones) of each polymer are created in the library to allow each solvent type to be combined with each polymer type. In addition to different solvent types, a variety of different ingredients (e.g., salts) may be placed in the solution, yet further expanding the array of choices for library analysis. Such applications find use in the generation and isolation of new pseudopolymorphs (solvates and salts) that may be used as drugs.

Crystals formed on each polymer are analyzed using any suitable method. In some embodiments, analysis is conducted directly on the polymer surface, without removing the crystals. In other embodiments, crystals are removed and analyzed. Analysis includes, but is not limited to, crystal structure analysis, analysis of spectroscopic, packing, density, thermodynamic, properties, kinetic, surface, and mechanical properties. In some embodiments, analysis includes functional analysis such as testing bioavailability or biological activity after administration to a test organism (e.g., an animal or plant). For example, in some embodiments, rapid screening is conducted using the D8 Discover with GADDS X-ray diffraction system (Bruker AXS, Madison, Wisc.) or similar systems.

Polymorphs identified in the screening method are compared to existing polymorphs. Where a new polymorph is identified, the polymorph is characterized to identify properties that differ from previously known polymorphs (e.g., to identify improved drugs). Known polymorphs generated using the systems and methods of the present invention also are compared to existing production methods to identify whether the polymer-based method of the present invention provides advantages over existing production methods (e.g., less expensive or easier to produce, greater purity, superior crystals, ability to produce from aqueous solution, etc.).

Polymorphs identified by the present invention can be produced in large quantities. In some embodiments, crystals are collected and used to seed further solutions of the compound. However, in some cases the presence of the polymer surface may be required to generate crystals. In such embodiments, large or multiple surfaces or vessels are provided with the polymer known to generate the crystal to allow large-scale production.

Polymorphs produced by the methods of the present invention may be used in the generation of pharmaceutical formulations (See examples below). The novel polymorphs identified increase the available choices for designing drugs with desired properties, both in biological activity and in handling. For example, in order for many drugs to take action, they must dissolve in the gut and be absorbed in the blood stream. In many cases the rate at which the drug dissolves can limit its effectiveness. The polymorphs of the present invention, either alone, or in combination with other forms of the drug find use in optimizing effectiveness, generally, or for particular patients or patient groups (e.g., age groups, genders, species, etc.). In some cases, the novel polymorphs provide advantages in shelf-life or the ability of the compound to be included in tablets (See e.g., Sun and Grant, Pharm. Res., 18:274 [2001]).

Illustrative examples demonstrating the effectiveness of the systems and methods of the present invention are provided below. These examples highlight several preferred embodiments of the present invention. However, the present invention is not limited to these particular examples.

A) Carbamazepine

The systems and methods of the present invention have been used to identify and produce a new form of carbamazepine. Carbamazepine is a drug widely prescribed anticonvulsant, trigeminal neuralgia therapy, and antimanic under the trade names EPITOL and TEGRETOL.

Carbamazepine has anticonvulsant properties that have been found useful in the treatment of psychomotor epilepsy and as an adjunct in the treatment of partial epilepsies, when administered in conjunction with other anticonvulsant drugs to prevent the possible generalization of the epileptic discharge. A mild psychotropic effect has been observed in some patients, which seems related to the effect of the carbamazepine in psychomotor or temporal lobe epilepsy. Carbamazepine relieves or diminishes the pain associated with trigeminal neuralgia often within 24 to 48 hours. Carbamazepine, given as a monotherapy or in combination with lithium or neuroleptics, has been found useful in the treatment of acute mania and the prophylactic treatment of bipolar (manic-depressive) disorders. Like other tricyclic compounds, carbamazepine has a moderate anticholinergic action that is responsible for some of its adverse effects.

Carbamazepine may suppress ventricular automaticity due to its membrane-depressant effect similar to that of quinidine and procainamide, associated with suppression of phase 4 depolarization of the heart muscle fiber. A number of investigators have reported a deterioration of EEG abnormalities with regard to focal alterations and a higher incidence of records with nil beta activity during carbamazepine-combined treatment.

The absorption of carbamazepine in man is relatively slow. When taken in a single oral dose, the carbamazepine tablets and chewable tablets yield peak plasma concentrations of unchanged carbamazepine within 4 to 24 hours. With respect to the quantity of carbamazepine absorbed, there is no clinically relevant difference between the various dosage forms.

When the carbamazepine controlled-release tablets are administered repeatedly, they yield a lower average maximal concentration of carbamazepine in the plasma, without a reduction in the average minimal concentration. This tends to result in a lower incidence of intermittent concentration-dependent adverse drug reactions. It also ensures that the plasma concentrations remain largely stable throughout the day, thereby making it possible to manage with a twice-daily dosage.

Carbamazepine is bound to serum proteins to the extent of 70 to 80%. The concentration of unchanged substance in the saliva reflects the non-protein-bound portion present in the serum (20 to 30%). The elimination half-life of unchanged carbamazepine in the plasma averages approximately 36 hours following a single oral dose, whereas after repeated administration, which leads to autoinduction of hepatic enzymes, it averages only 16 to 24 hours, depending on the duration of the medication. In patients receiving concomitant treatment with other enzyme-inducing anti-epileptic agents, half-life values averaging 9 to 10 hours have been found.

Only 2 to 3% of the dose, whether given singly or repeatedly, is excreted in the urine in unchanged form. The primary metabolite is the pharmacologically active 10,11-epoxide. In man, the main urinary metabolite of carbamazepine is the trans-diol derivative originating from the 10,11-epoxide; a small portion of the epoxide is converted into 9-hydroxymethyl-10-carbamoyl-acridan. Other important biotransformation products are various monohydroxylated compounds, as well as the N-glucuronide of carbamazepine.

The therapeutic range for the steady-state plasma concentration of carbamazepine generally lies between 4 and 10 mcg/mL. Indications for each major current application are as follows:

Trigeminal Neuralgia:

For the symptomatic relief of pain of trigeminal neuralgia only during periods of exacerbation of true or primary trigeminal neuralgia (tic douloureux). It should not be used preventively during periods of remission. In some patients, carbamazepine has relieved glossopharyngeal neuralgia. For patients who fail to respond to carbamazepine, or who are sensitive to the drug, recourse to other accepted measures should be considered. Carbamazepine is not a simple analgesic and should not be used to relieve trivial facial pains or headaches.

The initial daily dosage should be small; 200 mg taken in 2 doses of 100 mg each is recommended. Total daily dosage can be increased by 200 mg per day until relief of pain is obtained. This is usually achieved at a dosage between 200 and 800 mg daily, but occasionally up to 1200 mg per day may be necessary. As soon as relief of pain has been obtained and maintained, progressive reduction in dosage should be attempted until a minimum effective dosage is reached. Because trigeminal neuralgia is characterized by periods of remission, attempts should be made to reduce or discontinue the use of carbamazepine at intervals of not more than 3 months, depending upon the individual clinical course. Prophylactic use of the drug in trigeminal neuralgia is not recommended.

Treatment of Acute Mania and Prophylaxis in Bipolar (Manic-Depressive) Disorders:

Carbamazepine may be used as a monotherapy or as an adjunct to lithium in the treatment of acute mania or prophylaxis of bipolar (manic-depressive) disorders in patients who are resistant to or are intolerant of conventional antimanic drugs. Carbamazepine may be a useful alternative to neuroleptics in such patients. Patients with severe mania, dysphoric mania or rapid cycling who are non-responsive to lithium may show a positive response when treated with carbamazepine. It is important to note that these recommendations are based on extensive clinical experience and some clinical trials versus active comparison agents.

The initial daily dosage should be low, 200 to 400 mg/day, administered in divided doses, although higher starting doses of 400 to 600 mg/day may be used in acute mania. This dose may be gradually increased until patient symptomatology is controlled or a total daily dose of 1600 mg is achieved. Increments in dosage should be adjusted to provide optimal patient tolerability. The usual dose range is 400 to 1200 mg/day administered in divided doses. Doses used to achieve optimal acute responses and tolerability should be continued during maintenance treatment. When given in combination with lithium and neuroleptics, the initial dosage should be low, 100 to 200 mg daily, and then increased gradually. A dose higher than 800 mg/day is rarely required when given in combination with neuroleptics and lithium, or with other psychotropic drugs such as benzodiazepines.

Management of Psychomotor (Temporal Lobe) Epilepsy:

Carbamazepine has been found useful in the management of psychomotor (temporal lobe) epilepsy and, as an adjunct, in some patients with secondary or partial epilepsy with complex symptomatology or secondarily generalized seizures, when administered in combination with other antiepileptic medication. As an alternative medication in patients with generalized tonic-clonic seizures who are experiencing marked side effects or fail to respond to other anticonvulsant drugs.

Current forms of carbamazepine are not effective in controlling petit mal, minor motor, myoclonic and predominantly unilateral seizures, and do not prevent the generalization of epileptic discharge. Moreover, exacerbation of seizures may occasionally occur in patients with atypical absences.

A low initial daily dosage with a gradual increase in dosage is advised. Dosage should be adjusted to the needs of the individual patient. TEGRETOL tablets and chewtabs should be taken in 2 to 4 divided doses daily, with meals whenever possible. The controlled release characteristics of TEGRETOL CR reduce the daily fluctuations of plasma carbamazepine. TEGRETOL CR (either whole or, if so prescribed, only half a tablet) should be swallowed unchewed with a little liquid during or after a meal. These controlled release tablets should be prescribed as a twice-daily dosage. If necessary, 3 divided doses may be prescribed.

For adults and children over 12 years: Initially 100 to 200 mg once or twice a day depending on the severity of the case and previous therapeutic history. The initial dosage is progressively increased in divided doses, until the best response is obtained. The usual optimal dosage is 800 to 1200 mg daily. In rare instances, some adult patients have received 1600 mg. As soon as disappearance of seizures has been obtained and maintained, dosage should be reduced very gradually until a minimum effective dose is reached.

For children 6 to 12 years: Initially 100 mg in divided doses on the first day. Increase gradually by adding 100 mg per day until the best response is obtained. Dosage should generally not exceed 1000 mg daily. As soon as disappearance of seizures has been obtained and maintained, dosage should be reduced very gradually until a minimum effective dose is reached.

Exising forms of carbamazepine have the following contraindications and problems.

1) Should not be administered to patients with a history of hepatic disease, acute intermittent porphyria or serious blood disorder.

2) The drug should not be administered immediately before, in conjunction with, or immediately after an MAO inhibitor. When it seems desirable to administer carbamazepine to a patient who has been receiving an MAO inhibitor, there should be as long a drug-free interval as the clinical condition allows, but in no case should this be less than 14 days. Then the dosage of carbamazepine should be low initially, and increased very gradually.
3) Carbamazepine should not be administered to patients presenting AV heart block.
4) Carbamazepine should not be administered to patients with known hypersensitivity to carbamazepine or to any of the tricyclic compounds, such as amitriptyline, trimipramine, imipramine, or their analogues or metabolites, because of the similarity in chemical structure.
5) Although reported infrequently, serious adverse effects have been observed during the use of carbamazepine. Agranulocytosis and aplastic anemia have occurred in a few instances with a fatal outcome. Leukopenia, thrombocytopenia and hepatocellular and cholestatic jaundice have also been reported.
6) Long-term toxicity studies in rats indicated a potential carcinogenic risk.
7) In women of childbearing potential, carbamazepine should, whenever possible, be prescribed as monotherapy, because the incidence of congenital abnormalities in the offspring of women treated with more than one antiepileptic drug (e.g., valproic acid plus carbamazepine plus phenobarbitone and/or phenytoin) is greater than in those of women receiving a single antiepileptic.

The reactions that have been most frequently reported with carbamazepine are CNS (e.g., drowsiness, headache, unsteadiness on the feet, diplopia, dizziness), gastrointestinal disturbances (nausea, vomiting), as well as allergic skin reactions. These reactions usually occur only during the initial phase of therapy, if the initial dose is too high, or when treating elderly patients. They have rarely necessitated discontinuing carbamazepine therapy and can be minimized by initiating treatment at a low dosage.

The occurrence of CNS adverse reactions may be a manifestation of relative overdosage or significant fluctuation in plasma levels. In such cases it is advisable to monitor the plasma levels and possibly lower the daily dose and/or divide it into 3 to 4 fractional doses.

The more serious adverse reactions observed are the hematologic, hepatic, cardiovascular and dermatologic reactions, which require discontinuation of therapy. If treatment with carbamazepine has to be withdrawn abruptly, the changeover to another antiepileptic drug should be effected under cover of diazepam.

The following additional adverse reactions have been reported:

Hematologic:

Occasional or frequent: Leukopenia. Occasional: Eosinophilia, thrombocytopenia. Rare: Leukocytosis, lymphadenopathy. Isolated cases: Agranulocytosis, aplastic anemia, pure red cell aplasia, macrocytic anemia, acute intermittent porphyria, reticulocytosis, folic acid deficiency, thrombocytopenic purpura, and possibly hemolytic anemia. In a few instances, deaths have occurred.

Hepatic:

Frequent: Elevated gamma-GT (due to hepatic enzyme induction), usually not clinically relevant. Occasional: Elevated alkaline phosphatase. Rarely: elevated transaminases. Rare: Jaundice, hepatitis of cholestatic, parenchymal, hepatocellular, or mixed type. Isolated cases: Granulomatous hepatitis.

Dermatologic:

Occasional to frequent: Skin sensitivity reactions and rashes, erythematous rashes, urticaria. Rare: Exfoliative dermatitis and erythroderma, Stevens-Johnson syndrome, systemic lupus erythematosus-like syndrome. Isolated cases: toxic epidermal necrolysis (Lyell's syndrome), photosensitivity, erythema multiform and nodosum, skin pigmentation changes, pruritus, purpura, acne, diaphoresis, alopecia and neurodermatitis.

Neurologic:

Frequent: Vertigo, somnolence, ataxia and fatigue. Occasionally: An increase in motor seizures (see Indications), headache, diplopia, nystagmus, accommodation disorders (e.g., blurred vision). Rare: Abnormal involuntary disorders (e.g., tremor, asterixis, orofacial dyskinesia, choreoathetosis disorders, dystonia, tics). Isolated cases: Oculomotor disturbances, speech disorders (e.g., dysarthria or slurred speech), peripheral neuritis, paresthesia. There have been some reports of paralysis and other symptoms of cerebral arterial insufficiency but no conclusive relationship to the administration of carbamazepine could be established.

Cardiovascular:

Disturbances of cardiac conduction, bradycardia, arrhythmias, Stokes-Adams in patients with AV block, congestive heart failure, hypertension or hypotension aggravation of coronary artery disease, thrombophlebitis, thromboembolism. Some of these complications (including myocardial infarction and arrhythmia) have been associated with other tricyclic compounds.

Psychiatric:

Isolated cases: Hallucinations (visual or acoustic), depression, sometimes with talkativeness, agitation, loss of appetite, restlessness, aggressive behaviour, confusion, activation of psychosis.

Genitourinary:

Isolated cases: Interstitial nephritis and renal failure, as well as signs of renal dysfunction (e.g., albuminuria, glycosuria, hematuria, oliguria sometimes associated with elevated blood pressure, and elevated BUN/azotemia), urinary frequency, urinary retention and renal failure. Isolated reports: Sexual disturbances/impotence.

Gastrointestinal:

Occasional or frequent: Nausea, vomiting. Occasional: Dryness of the mouth and throat. Rare: Diarrhea or constipation. Isolated cases: Abdominal pain, glossitis, stomatitis, anorexia.

Sense Organs:

Isolated cases: Lens opacities, conjunctivitis, retinal changes, tinnitus, hyperacusis and taste disturbances.

Endocrine System and Metabolism:

Occasionally edema, fluid retention, weight increase, hyponatremia and reduced plasma osmolality due to antidiuretic hormone (ADH)-like effect occurs, leading in isolated cases to water intoxication accompanied by lethargy, vomiting, headache, mental confusion and neurological abnormalities. Isolated cases of gynecomastia or galactorrhea have been reported, as well as abnormal thyroid function tests (decreased L-thyroxine, i.e., FT(4), T(4), T(3), and increased TSH, usually without clinical manifestations), disturbances of bone metabolism (decrease in plasma calcium and 25-OH-calciferol), leading in isolated cases to osteomalacia, as well as reports of elevated levels of cholesterol, including HDL cholesterol and triglycerides.

Musculoskeletal:

Isolated cases: Arthralgia, muscle pain or cramp.

Respiratory:

Isolated cases: Pulmonary hypersensitivity characterized by fever, dyspnea, pneumonitis or pneumonia.

Hypersensitivity:

A rare delayed multi-organ hypersensitivity disorder with fever, skin rashes, vasculitis, lymphadenopathy, disorders mimicking lymphoma, arthralgia, leukopenia, eosinophilia, hepato-splenomegaly and abnormal liver function tests, occurring in various combinations. Other organs may also be affected (e.g., lungs, kidneys, pancreas, myocardium). Isolated cases: Aseptic meningitis, with myoclonus and eosinophilia; anaphylactic reaction. Treatment should be discontinued should such hypersensitivity reactions occur.

The polymorph of carbamazepine identified by the present invention may have less adverse effects or may allow better management of adverse effects (e.g., because of bioavailabilty) than currently available polymorphs when used alone, or in combination with other polymorphs. Side-by-side comparisons in humans or animal models are carried out to determine differences of interest. The following tests find use in comparing carbamazepine treatments:

Bone Marrow Function:

Complete blood counts, including platelets and possibly reticulocytes and serum iron, should be carried out before treatment is instituted. Suggested guidelines for monitoring are weekly for the first month, then monthly for the next 5 months, thereafter 2 to 4 times a year.

Differences in white blood cell or platelet counts are observed during treatment as well as monitoring for nonprogressive fluctuating asymptomatic leukopenia, fever or sore throat, rash, ulcers in the mouth, easy bruising, petechial or purpuric hemorrhage.

Hepatic Function:

Baseline and periodic evaluations of hepatic function are performed, particularly in elderly patients and patients with a history of liver disease.

Kidney Function:

Pretreatment and periodic complete urinalysis and BUN determinations should be performed.

Ophthalmic Examinations:

Carbamazepine has been associated with pathological eye changes. Periodic eye examinations, including slit-lamp funduscopy and tonometry, are conducted.

Plasma Levels:

Monitoring plasma levels finds use in tracking the following conditions: dramatic increase in seizure frequency/verification of patient compliance; during pregnancy; when treating children or adolescents; in suspected absorption disorders; in suspected toxicity, especially where more than one drug is being used (i.e., adverse drug interactions).

Increased Seizure Frequency:

Seizure frequency is monitored.

Dermatologic:

Mild skin reactions, e.g. isolated macular or maculopapular exanthema, usually disappear within a few days or weeks, either during continued course of treatment or following a decrease in dosage. However, the patient is observed for the rare possibility of Stevens-Johnson syndrome or Lyell's syndrome occurring.

Occurrence of Behavioral Disorders:

Because it is closely related to the other tricyclic drugs, there is some possibility that carbamazepine might activate a latent psychosis, or, in elderly patients, produce agitation or confusion, especially when combined with other drugs.

Drug Interactions:

Induction of hepatic enzymes in response to carbamazepine may have the effect of diminishing or abolishing the activity of certain drugs that are also metabolized in the liver. The dosage of the following drugs may have to be adjusted when administered with carbamazepine: Clobazam, clonazepam, ethosuximide, primidone, valproic acid, alprazolam, corticosteroids (e.g. prednisolone, dexamethasone), cyclosporin, digoxin, doxycycline, felodipine, haloperidol, thioridazine, imipramine, methadone, oral contraceptives, theophylline and oral anticoagulants (warfarin, phenprocoumon, dicumarol). Phenytoin plasma levels have been reported both to be raised and to be lowered by carbamazepine, and mephenytoin plasma levels have been reported in rare instances to increase. The following drugs have been shown to raise plasma carbamazepine levels: erythromycin, troleandomycin, possibly josamycin, isoniazid, verapamil, diltiazem, propoxyphene, viloxazine, fluoxetine, cimetidine, acetazolamide, danazol and possibly desipramine. Nicotinamide raises carbamazepine plasma levels in children, but only at high dosage in adults. Since an increase in carabamazepine plasma levels may result in unwanted effects (e.g., dizziness, drowsiness, ataxia, diplopia and nystagmus), the blood levels should be monitored.

The plasma levels of carbamazepine may be reduced by phenobarbitone, phenytoin, primidone, progabide or theophylline and possibly by clonazepam. On the other hand, valproic acid, valpromide and primidone have been reported to raise plasma levels of the pharamacologically active metabolite, carbamazepine-10,11 epoxide.

Combined use of carbamazepine with lithium, metoclopramide or haloperidol may increase the risk of neurotoxic side effects (even in the presence of therapeutic plasma levels). Concomitant use of carbamazepine and isoniazid has been reported to increase isoniazid-induced hepatotoxicity. Carbamazepine, like other anticonvulsants, may adversely affect the reliability of oral contraceptives; breakthrough bleeding may occur. Concomitant medication with carbamazepine and some diuretics (hydrochlorothiazide, furosemide) may lead to symptomatic hyponatremia. Carbamazepine may antagonize the effects of non-depolarizing muscle relaxants (e.g., pancuronium); their dosage may need to be raised and patients should be monitored closely for more rapid recovery from neuromuscular blockade than expected. Isotretinoin has been reported to alter the bioavailability and/or clearance of carbamazepine and its active 10,11-epoxide; carbamazepine plasma levels should be monitored.

Carbamazepine is currently supplied as in the following forms as TEGRETOL (All TEGRETOL products are alcohol-free, bisulfite-free, gluten-free, lactose-free, parabens-free and tartrazine-free.):

200 mg:

Each round, white, flat, bevel-edged, double-scored tablet, engraved GEIGY on one side, contains: Carbamazepine 200 mg. Energy: Nil. Sodium: <1 mmol (0.3 mg). Bottles of 100 and 500. Protect from heat (store below 30° C.) and humidity.

Chewtabs 100 mg:

Each pale pink, round, flat, bevel-edged tablet with distinct red spots, and GEIGY engraved on one side and MR on the other with the tablet fully bisected between the M and R, contains: Carbamazepine 100 mg. Energy: 4.5 kJ (1.08 kcal). Sodium: <1 mmol (0.12 mg). Bottles of 100. Protect from heat (store below 30° C.), light and humidity.

Chewtabs 200 mg:

Each pale pink, oval biconvex tablet with distinct red spots, and GEIGY engraved on one side and PU on the other with the tablet fully bisected between the P and the U, contains:

Carbamazepine 200 mg. Energy: 8.9 kJ (2.12 kcal). Sodium: <1 mmol (0.12 mg). Bottles of 100. Protect from heat (store below 30° C.), light and humidity.

CR 200 mg:

Each beige-orange, oval, slightly biconvex, film-coated tablet, engraved CG on one side and HC on the other and fully bisected on both sides, contains: Carbamazepine 200 mg. Energy: Nil. Sodium: 0.09 mmol (2.1 mg). Bottles of 100. Protect from heat (store below 25° C.) and humidity.

CR 400 mg:

Each brownish-orange, oval, slightly biconvex tablet, engraved CG/CG on one side and ENE/ENE on the other and fully bisected on both sides, contains: Carbamazepine 400 mg. Energy: Nil. Sodium: 0.19 mmol (4.3 mg). Bottles of 100. Protect from heat (store below 25° C.) and humidity.

The crystallization of carbamazepine has been thoroughly characterized by nearly one hundred publications in the literature, and its bioavailability has been demonstrated to depend on the polymorph administered (Kobayashi et al., Int. J. Pharm., 193:137 [2000]). The most stable of the known polymorphs at room temperature is a monoclinic form in the space group $P2_1/c$ with lattice parameters a=7.534, b=11.150, c=13.917, β=92.94 (Lisgarten et al., J. Crystallographic and Spectroscopic Res. 19:641 [1989]). The molecules pack as hydrogen bonded dimmers through the carboxamide group with an anti (centrosymmetric) relationship. The trigonal form has also been analyzed by single crystal X-ray diffraction and crystallizes in the space group R3 with a=35.454, c=5.253, γ=120 (Lowes et al., J. Pharm. Sci., 76:744 [1987]). Though the molecules form very similar dimmers to the monoclinic form, the packing of the dimmers around a threefold screw axis leads to a more open structure (density at room temperature is 1.235 g/cm$^3$ for trigonal and 1.343 g/cm$^3$ for the monoclinic). A triclinic form, which can be formed by sublimation, has been characterized by powder X-ray diffraction. Indexing of the powder pattern is consistent with the following lattice parameters: a=20.61, b=5.24, c=22.30, α=89.4, β=84.5, γ=85.5 (Ceolin et al., J. Pharm. Sci., 86:1062 [1997]). Assuming eight molecules in the unit cell gives a calculated density at room temperature of 1.31 g/cm$^3$. The relationship between these three forms has been studied in detail and it is observed that upon melting, the monoclinic form converts to the triclinic (Behme and Brooke, J. Pharm. Sci., 80:986 [1991]). At room temperature, the trigonal form undergoes solvent-mediated conversion to the monoclinic crystal as is easily observed by its transformation from a needle-like morphology to large prisms.

With the goal of generating a fourth polymorph of carbamazepine, crystallization was carried out using the systems and methods of the present invention in the presence of a commercial set of polymers. Approximately 10 mg of each polymer was placed in a 96-well polypropylene plate. To each of these wells was added 300 μL of a 70 mM solution of carbamazepine in methanol. The plate was loosely covered and the solvent allowed to evaporate slowly at room temperature. Each well was then examined under a microscope and the morphology of the crystals was assessed. The wells containing hydroxypropyl cellulose (Mw=60,000, Scientific Polymer Products, Inc., Ontario, N.Y.) and poly(4-methylpentene) produced crystals that were blocky and these, along with samples of the stable monoclinic crystals grown in other wells of the library were subjected to unit cell determinations on a Bruker SMART diffractometer. Subsequent studies showed that poly(α-methylstyrene) and poly(p-phenylene ether-sulfone) also produced these blocky crystals.

All crystals tested were monoclinic; however the two samples of the blocky crystals displayed unit cell parameters that were easily distinguishable from all other polymorphs. Collection of a full set on one of these crystals confirmed that, even in the case of this very well studied pharmaceutical, a new polymorph had been obtained. Carbamazepine was induced to crystallize in a C-centered monoclinic cell in the space group C2/c. Cell parameters were a=26.609 Å, b=6.927 Å, c=13.957 Å, β=109.702°and the density was 1.296 g/cm$^3$ (158 K.). The structure is easily distinguishable from the known monoclinic form that crystallizes in a primitive cell, one having lattice points only at the corner of the unit cell. The molecules pack as hydrogen-bonded dimers through the carboxamide group with an anti relationship (See, FIG. 1). Though the conformation of the molecules within the dimers is similar between all three polymorphs, substantial differences exist between the packing of these units. The oxygen of the new polymorph is engaged in two short intermolecular hydrogen bonds. The closest contact between the normalized (1.083 Å for carbon, 1.009 Å for nitrogen) position of the hydrogen on the urea syn to the oxygen of the carbonyl is 1.86 Å. This distance is similar to that in the primitive monoclinic polymorph (1.92 Å). However, in the new polymorph the carbonyl is only 2.28 Å from a vinylic proton in the seven-membered ring while the corresponding value is 2.48 Å in the primitive monoclinic form. The hydrogen on the urea anti to the oxygen of the carbonyl is >2.7 Å from an aromatic carbon and is similar in both cases.

The infrared spectrum for the primitive monoclinic form shows absorptions at 3466, 3161, 1677, 1386, and 767 cm$^{-1}$ in agreement with literature values (Rustichelli et al., J. Pharm. Biomed. Anal., 23:41 [2000]). The corresponding peaks in the new polymorph are found at 3474, 3149, 1674, 1394, 773, and 765 cm$^{-1}$. Similar results were found using infrared microscopy of single crystals and KBr pellets produced at 10,000 psi indicating that a phase transformation under pressure (Kala et al., Pharmazie 41:61 [1986]; Kala et al., Pharmazie 41:777 [1986]; and Kala et al., Pharmazie 42:524 [1987]) was not taking place. Significant differences in the IR spectra of two different polymorphs provide a fast, reliable method of polymorph characterization despite the fact that a hydrogen-bonded dimer is observed in the crystal structure of both polymorphs. Differential scanning calorimetry shows an absence of phase transitions below 184° C. at a scan rate of 10° C./minute where the new polymorph melts with partial transformation. Therefore, it is contemplated that this new form has good shelf life (kinetic trapping of the unstable form).

Experiments conducted during the development of the present invention have provided a scale-up production method for the new C-centered monoclinic form of carbamazepine. Seeding of a supersaturated carbamazepine solution with crystals produced on the polymer successfully provided gram quantities of the new polymorph. Because seeding is commonly employed in an industrial setting (Beckmann, Org. Process Res. Dev., 4:372 [2000]), this is a suitable approach for producing large quantities of polymorphs without requiring a polymer substrate to promote growth once the novel polymorph has been discovered. In addition, more traditional strategies for controlling crystallization by, for example, using designed additives to control polymorph production can be applied based on the lattice parameters and preferred growth directions of the new form.

A previous report of a fourth form of carbamazepine (Kala et al., Acta Pharm. Technol., 32:72 [1986]), obtained by cooling a solution of 2.0 g of carbamazepine in 100 mL of ethyl acetate to −18° C., has not been generally accepted in the art. The Kala et al. method was repeated, yielding crystals that by morphology and powder X-ray diffraction were identical with independently synthesized trigonal material. Furthermore, the three diffraction peaks that were assigned as diagnostic of the Kala polymorph were present in both samples and sensitive to sample orientation. Therefore, the Kala method does not produce the C-centered monoclinic carbamazepine crystals obtained using the systems and methods of the present invention.

B. Acetaminophen

The systems and methods of the present invention were used to obtain orthorhombic acetaminophen.

Figure 2:
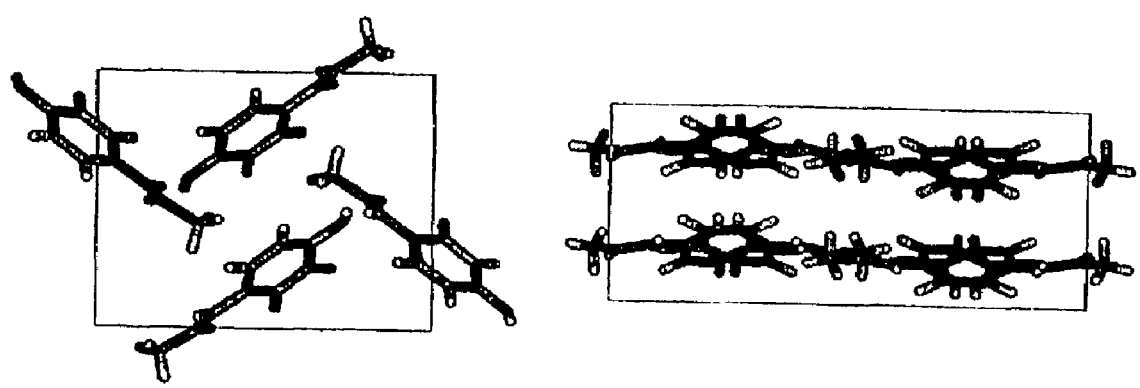
FIG. 2 shows a view down the a-axis of the monoclinic (commercial, left, mp 170° C.) and orthorhombic (right, mp 160° C.) forms of acetaminophen illustrating the differences in molecular packing.

The importance of polymorph control is best illustrated by examples from the pharmaceutical industry, which frequently deals with solid forms other than the most stable crystalline polymorph, metastable thermodynamic states (Rodriguez and Murphy, J. Pharm. Sci., 88:651 [1999]; Bryn et al., Chem. Mat., 6:1148 [1994]; Caira, In Design of Organic Solids, Vol. 198:163 [1998]; and Brittain, supra.). The Food and Drug Administration (FDA) typically approves only a specific polymorph of a drug for distribution rather than a particular substance because of the profound effect of solid-state form on key properties such as shelf life, dissolution rate, and equilibrium solubility (Byrn et al., Pharm. Res., 12:945 [1995]). The analgesic acetaminophen (4-acetamidophenol) is an example of a common drug which gives rise to multiple polymorphs (Haisa et al., Acta Crystallogr. Sect. B-Struct. Sci., B30:2510 [1974]; Haisa et al., Acta Crystallogr. Sect. B-Struct. Sci., 32:1283 [1976]; and Naumov et al., Acta Crystallogr. Sect. C-Cryst. Struct. Commun., 54:653 [1998]). The solid-state structure of two of these are shown in FIG. 2. The packing patterns are dramatically different and this results in differing melting points and solubility of the crystals.

Both monoclinic (Haisa et al., 1976, supra; and Naumov et al., supra) and orthorhombic (Haisa et al., 1974, supra) forms of acetaminophen have been described in the literature accompanied by sporadic reports of a third, extremely unstable phase (Di Martino et al., J. Therm. Anal., 48:447 [1997]). The commercial tablets are composed of the thermodynamically most stable (Sacchetti, J. Thermal Analysis and Calorimetry, 63:345 [2000]) monoclinic polymorph despite the fact that direct compression into tablets is not possible with this form (Nichols and Frampton, J. Pharm. Sci., 87:684 [1998]). However, the orthorhombic modification possesses the requisite slip planes in the crystal structure to allow for plastic deformation and thus direct tabletting. Therefore the choice to use the monoclinic form commercially likely results from the difficulty associated with producing pure samples of the more soluble orthorhombic polymorph. Methods for producing this less stable form are thus of considerable interest yet efforts to produce this form exclusively from solution have met with repeated failure (Naumov et al., supra; Nichols and Frampton, supra; and Di Martino et al., Int. J. Pharm., 128:1 [1996]). Pure orthorhombic material can only be obtained by crystallization from melted monoclinic crystals under an inert atmosphere.(Di Martino et al., 1996, supra).

Commercially, acetaminophen (APAP, paracetamol) is sold in the United States under trade names including, ACETA ELIXIR 1, ACETA TABLETS 1, ACETAMINOPHEN UNISERTS 1, ACTAMIN 1, ACTAMIN EXTRA 1, ACTAMIN SUPER 2, AMINOFEN 1, APACET ELIXIR 1, APACET EXTRA STRENGTH CAPLETS 1, APACET EXTRA STRENGTH TABLETS 1, APACET, INFANTS' 1, APACET REGULAR STRENGTH TABLETS 1, ASPIRIN FREE ANACIN MAXIMUM STRENGTH CAPLETS 1, ASPIRIN FREE ANACIN MAXIMUM STRENGTH GEL CAPLETS 1, ASPIRIN FREE ANACIN MAXIMUM STRENGTH TABLETS 1, ASPIRIN-FREE EXCEDRIN CAPLETS 2, BANESIN 1, BAYER SELECT MAXIMUM STRENGTH HEADACHE PAIN RELIEF FORMULA 2, DAPA 1, DAPA X-S 1, DATRIL EXTRA-STRENGTH 1, FEVERALL, CHILDREN's 1, FEVERALL, INFANTS' 1, FEVERALL JUNIOR STRENGTH 1, FEVERALL SPRINKLE CAPS, CHILDREN's 1, FEVERALL SPRINKLE CAPS JUNIOR STRENGTH 1, GENAPAP CHLDREN's ELIXIR 1, GENAPAP CHILDREN's TABLETS 1, GENAPAP EXTRA STRENGTH CAPLETS 1, GENAPAP EXTRA STRENGTH TABLETS 1, GENAPAP, INFANTS' 1, GENAPAP REGULAR STRENGTH TABLETS 1, GENEBS EXTRA STRENGTH CAPLETS 1, GENEBS REGULAR STRENGTH TABLETS 1, GENEBS X-TRA 1, LIQUIPRIN CHILDREN's ELIXIR 1, LIQUIPRIN INFANTS' DROPS 1, NEOPAP 1, ORAPHEN-PD 1, PANADOL, CHLDREN's 1, PANADOL, INFANTS' 1, PANADOL JUNIOR STRENGTH CAPLETS 1, PANADOL MAXIMUM STRENGTH CAPLETS 1, PANADOL MAXIMUM STRENGTH TABLETS 1, PHENAPHEN CAPLETS 1, REDUTEMP 1, SNAPLETS-FR 1, ST. JOSEPH ASPIRIN-FREE FEVER REDUCER FOR CHLDREN 1, SUPPAP-120 1, SUPPAP-325 1, SUPPAP-650 1, TAPANOL EXTRA STRENGTH CAPLETS 1, TAPANOL EXTRA STRENGTH TABLETS 1, TEMPRA 1, TEMPRA D.S 1, TEMPRA, INFANTS' 1, TEMPRA SYRUP 1, TYLENOL ARTHRITIS EXTENDED RELIEF, TYLENOL CHILDREN's CHEWABLE TABLETS 1, TYLENOL CHILDREN's ELIXIR 1, TYLENOL CHILDREN's SUSPENSION LIQUID 1, TYLENOL EXTRA-STRENGTH ADULT LIQUID PAIN RELIEVER 1, TYLENOL EXTRA STRENGTH CAPLETS 1, TYLENOL EXTRA STRENGTH GELCAPS 1, TYLENOL EXTRA STRENGTH TABLETS 1, TYLENOL INFANTS' DROPS 1, TYLENOL INFANTS' SUSPENSION DROPS 1, TYLENOL JUNIOR STRENGTH CAPLETS 1, TYLENOL JUNIOR STRENGTH CHEWABLE TABLETS 1, TYLENOL REGULAR STRENGTH CAPLETS 1, TYLENOL REGULAR STRENGTH TABLETS 1, VALORIN 1, and VALORIN EXTRA 1.

Acetaminophen is used to relieve pain and reduce fever. Unlike aspirin, it does not relieve the redness, stiffness, or swelling caused by rheumatoid arthritis. However, it may relieve the pain caused by mild forms of arthritis. This medicine is available without a prescription.

Acetaminophen is available in the following dosage forms: oral capsules, granules (in packets), liquid, powders (in capsules), suspensions, tablets, and chewable tablets; acetaminophen/caffeine tablets; and rectal suppositories.

The dose of acetaminophen is different for different patients. For oral dosage forms (capsules, granules, powders, solution, suspension, or tablets) and rectal dosage forms (suppositories):

For pain or fever:

Adults and teenagers—325 or 500 milligrams (mg) every three or four hours, 650 mg every four to six hours, or 1000 mg every six hours as needed. For short-term treatment (up to ten days), the total dose should not be more than 4000 mg (for example, eight 500-mg tablets) a day. For long-term treatment, the total dose should not be more than 2600 mg (for example, eight 325-mg tablets) a day.

Children—Acetaminophen dose is based on the child's age.

Infants up to 3 months of age: 40 mg every four hours as needed.

Infants 4 to 12 months of age: 80 mg every four hours as needed.

Children 1 to 2 years of age: 120 mg every four hours as needed.

Children 2 to 4 years of age: 160 mg every four hours as needed.

Children 4 to 6 years of age: 240 mg every four hours as needed.

Children 6 to 9 years of age: 320 mg every four hours as needed.

Children 9 to 11 years of age: 320 to 400 mg every four hours as needed.

Children 11 to 12 years of age: 320 to 480 mg every four hours as needed.

The systems and methods of the present invention were used to develop an efficient method of producing orthorhombic acetaminophen from solution. Solutions were exposed to a polymer library containing acrylonitrile/butadiene/styrene resin, alginic acid (sodium salt), butyl/isobutyl methacrylate copolymer, cellulose acetate, cellulose acetate butyrate, cellulose propionate, cellulose triacetate, ethyl cellulose, ethylene/acrylic acid copolymer, ethylene/ethyl acrylate copolymer, ethylene/propylene copolymer, ethylene/vinyl acetate (14, 18, 25, 28, 33% and 40% VA) copolymer, hydroxybutyl methyl cellulose, hydroxypropyl cellulose, hydroxypropyl methyl cellulose, methyl cellulose, methyl vinyl ether/maleic acid copolymer, methyl vinyl ether/maleic anhydride copolymer, nylon 6, nylon 6/6, nylon 6/9, nylon 6/10, nylon 6/12, nylon 6(3)T, nylon 11, nylon 12, phenoxy resin, polyacetal, polyacrylamide, polyacrylamide carboxyl modified (low), polyacrylamide carboxyl modified (high), poly(acrylic acid), polyamide resin, 1,2-polybutadiene, poly(1-butene) isotactic, poly(n-butyl methacrylate), polycarbonate resin, poly(diallyl isophthalate), poly(diallyl phthalate), poly(2,6-dimethylphenylene oxide), poly(4,4-dipropoxy-2,2-diphenyl propane fumarate), poly(ethyl methacrylate), polyethylene high density, polyethylene low density, polyethylene chlorinated (25, 36, 42, and 48% chlorine), polyethylene chlorosulfonated, poly(ethylene oxide), polyethylene oxidized, poly(ethylene terephthalate), poly(2-hydroxyethyl methacrylate), poly(isobutyl methacrylate), polyisoprene chlorinated, poly(methyl methacrylate), poly(4-methyl-1-pentene), poly(alpha-methylstyrene), poly(p-phenylene ether-sulphone), poly(phenylene sulfide), polypropylene isotactic chlorinated, polypropylene isotactic, polystyrene, polysulfone resin, poly(tetrafluoroethylene), poly(2,4,6-tribromostyrene), poly(vinyl acetate), poly(vinyl alcohol) 100% hydrolyzed, poly(vinyl alcohol) 98% hydrolyzed, poly(vinyl buyral), poly(vinyl chloride), poly(vinyl chloride) 1.8% carboxylated, poly(vinyl formal), polyvinylpyrrolidone, poly(vinyl stearate), poly(vinylidene fluoride), styrene/acrylonitrile copolymer (75/25), styrene/acrylonitrile copolymer (70/30), styrene/allyl alcohol copolymer, styrene/butadiene ABA block copolymer, styrene/butyl methacrylate copolymer, styrene/ethylene-butylene ABA block copolymer, styrene/maleic anhydride copolymer, vinyl alcohol/vinyl butyral copolymer, vinyl chloride/vinyl acetate (10, 12, and 19% VA) copolymer, vinyl chloride/vinyl acetate copolymer 1% carboxylated, vinyl chloride/vinyl acetate/hydroxypropyl acrylate terpolymer, and vinyl chloride/vinyl acetate/vinyl alcohol terpolymer using 96-well plates. The crystals were grown by cooling a solution of acetaminophen (4.8 mg) in hot water (300 μL) in each unique well. In the absence of polymers, these conditions would be expected to yield monoclinic acetaminophen. However, with the present invention, there is a significant bias toward the production of orthorhombic acetaminophen when crystallizations are carried out in the presence of Nylons or halogenated polymers such as perfluoroethylene, chlorinated polyethylene, and tribromostyrene. Since these polymers show no water solubility, it can be assumed that interaction occurs at the polymer surface. This method of crystal growth was successfully scaled up by crystallization in glass vials with Nylon 11 to produce gram quantities of material that was proven to be pure orthorhombic by powder X-ray diffraction.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method for identifying crystals by exposing a sample comprising a solution containing a compound to a plurality of different surfaces to generate and identify different crystal forms of said compound, comprising:
   a) providing:
      i) a sample comprising a solution containing a compound; and
      ii) a polymer library comprising two or more different polymers on a solid support, wherein each of said two or more different polymers is on a separate zone of said solid support;
   b) simultaneously contacting said two or more different polymers on said solid support of said polymer library with said solution under conditions such that said two or more different polymers are undissolved in said solution so as to facilitate crystal formation, and wherein said crystals are formed on the surface of said two or more different polymers;
   c) identifying crystals formed in the presence of said polymers;
   d) analyzing said crystals formed in the presence of said polymers.

2. The method of claim 1, wherein said sample comprises a melt.

3. The method of claim 1, wherein said sample comprises a vapor.

4. The method of claim 1, wherein said compound comprises a drug.

5. The method of claim 1, wherein said compound comprises a pigment.

6. The method of claim 1, wherein said compound comprises an explosive.

7. The method of claim 1, wherein said compound comprises a nonlinear optical crystal.

8. The method of claim 1, wherein said compound comprises a solid-state reactive compound.

9. The method of claim 1, wherein said compound is selected from the group consisting of organic compounds, inorganic compounds, and organometallic compounds.

10. The method of claim 1, wherein said polymers are selected from the group consisting of acrylonitrile/butadiene/styrene resin, alginic acid (sodium salt), butyl/isobutyl methacrylate copolymer, cellulose acetate, cellulose acetate butyrate, cellulose propionate, cellulose triacetate, ethyl cellulose, ethylene/acrylic acid copolymer, ethylene/ethyl acrylate copolymer, ethylene/propylene copolymer, ethylene/vinyl acetate (14, 18, 25, 28, 33% and 40% VA) copolymer, hydroxybutyl methyl cellulose, hydroxypropyl cellulose, hydroxypropyl methyl cellulose, methyl cellulose, methyl vinyl ether/maleic acid copolymer, methyl vinyl ether/maleic anhydride copolymer, nylon 6, nylon 6/6, nylon 6/9, nylon 6/10, nylon 6/12, nylon 6(3)T, nylon 11, nylon 12, phenoxy resin, polyacetal, polyacrylamide, polyacrylamide carboxyl modified (low), polyacrylamide carboxyl modified (high), poly(acrylic acid), polyamide resin, 1,2-polybutadiene, poly (1-butene) isotactic, poly(n-butyl methacrylate), polycarbonate resin, poly(diallyl isophthalate), poly(diallyl phthalate), poly(2,6-dimethyl-p-phenylene oxide), poly(4,4-dipropoxy-2,2-diphenyl propane fumarate), poly(ethyl methacrylate), polyethylene high density, polyethylene low density, polyethylene chlorinated (25, 36, 42, and 48% chlorine), polyethylene chlorosulfonated, poly(ethylene oxide), polyethylene oxidized, poly(ethylene terephthalate), poly(2-hydroxyethyl methacrylate), poly(isobutyl methacrylate), polyisoprene chlorinated, poly(methyl methacrylate), poly(4-methyl-1-pentene), poly(alpha-methylstyrene), poly(p-phenylene ether-sulphone), poly(phenylene sulfide), polypropylene isotactic chlorinated, polypropylene isotactic, polystyrene, polysulfone resin, poly(tetrafluoroethylene), poly(2,4,6-tribromostyrene), poly(vinyl acetate), poly(vinyl alcohol) 100% hydrolyzed, poly(vinyl alcohol) 98% hydrolyzed, poly (vinyl buyral), poly(vinyl chloride), poly(vinyl chloride) 1.8% caeboxylated, poly(vinal formal), polyvinylpyrrolidone, poly(vinyl stearate), poly(vinylidene fluoride), styrene/acrylonitrile copolymer (75/25), styrene/acrylonitrile copolymer (70/30), styrene/allyl alcohol copolymer, styrene/butadiene ABA block copolymer, styrene/butyl methacrylate copolymer, styrene/ethylene-butylene ABA block copolymer, styrene/maleic anhydride copolymer, vinyl alcohol/vinyl butyral copolymer, vinyl chloride/vinyl acetate (10, 12, and 19% VA) copolymer, vinyl chloride/vinyl acetate copolymer 10o carboxylated, vinyl chloride/vinyl acetate/hydroxypropyl acrylate terpolymer, and vinyl chloride/vinyl acetate/vinyl alcohol terpolymer, functionalized polybutadienes, poly(ethylene-co-propylene-co-5-methylene-2-norbornene), poly(perfluoropropylene oxide)-co-poly(perfluoroformaldehyde), metaldehyde, pectic acid, polyethylenimine, poly(ethylene-co-carbon monoxide), poly(3-hydroxybutyric acid), poly(dimethylsiloxane), poly[(dibenzo-18-crown-6)-co-formaldehyde], poly[(phenyl isocyanate)-co-formaldehyde], poly(vinylsulfonic acid), poly(melamine-co-formaldehyde), polyphosphates, polyphosphazenes, tributyltin fluoride, and polysaccharides.

11. The method of claim 1, wherein said plurality of different polymers comprises 3 or more different polymers.

12. The method of claim 1, wherein said plurality of different polymers comprises 10 or more different polymers.

13. The method of claim 1, wherein said plurality of different polymers comprises 50 or more different polymers.

14. The method of claim 1, further comprising the step of isolating at least one of said formed crystals and seeding a second sample comprising said compound with said one or more formed crystals to generate bulk crystals.

15. The method of claim 14, further comprise the step of formulating said bulk crystals into a pharmaceutical preparation.

16. The method of claim 15, further comprising the step of treating a subject with said pharmaceutical preparation.

17. The method of claim 1, further comprising the step of identifying a polymer from among said plurality of polymers that generates said formed crystals.

18. The method of claim 1, wherein said crystals formed on the surface of said polymers are removed from the surface of said polymers.

19. The method of claim 1, wherein said solid surface is selected from the group consisting of a plate surface, a glass surface, a metal surface, a ceramic surface, a multi-well plate, a dish, a vial, a tube, and a flask.

20. The method of claim 19, wherein said solid surface comprises a series of containers.

21. The method of claim 1, wherein said two or more different polymers are attached on said solid support.

22. The method of claim 1, wherein said crystal formation is facilitated through said two or more different polymers providing a nucleating surface.

23. A method for preparing crystals for use in a pharmaceutical preparation comprising:
   a) providing:
      i) a solution comprising a dissolved drug; and
      ii) an identified polymer of claim 17; and
   b) contacting said polymer with said dissolved drug to generate crystallized drug.

24. The method of claim 23, further comprising the step of formulating said crystallized drug into a pharmaceutical preparation.

25. The method of claim 24, further comprising the step of treating a subject with said pharmaceutical preparation.

* * * * *

UNITED STATES PATENT AND TRADEMARK OFFICE
CERTIFICATE OF CORRECTION

| | |
|---|---|
| PATENT NO. | : 7,429,238 B2 |
| APPLICATION NO. | : 10/269190 |
| DATED | : September 30, 2008 |
| INVENTOR(S) | : Adam J. Matzger |

It is certified that error appears in the above-identified patent and that said Letters Patent is hereby corrected as shown below:

Title Page 1 at (75) Inventors, delete inventors Meidong Lang and Kibum Kim. The sole inventor should read --Adam J. Matzger, Ann Arbor, MI (US)--.

Signed and Sealed this

Twenty-seventh Day of January, 2009

JOHN DOLL
*Acting Director of the United States Patent and Trademark Office*